United States Patent [19]

Forte

[11] Patent Number: 5,191,152
[45] Date of Patent: Mar. 2, 1993

[54] PROCESS FOR THE SEPARATION OF AROMATIC HYDROCARBONS WITH ENERGY REDISTRIBUTION

[75] Inventor: Paulino Forte, Yonkers, N.Y.

[73] Assignee: UOP, Des Plaines, Ill.

[21] Appl. No.: 657,923

[22] Filed: Feb. 20, 1991

[51] Int. Cl.$^5$ ............................................. C07C 7/10
[52] U.S. Cl. ................................. 585/833; 585/804; 585/834
[58] Field of Search .................. 585/833, 834, 804; 203/21, 25; 208/334

[56] References Cited

U.S. PATENT DOCUMENTS

| | | | |
|---|---|---|---|
| 3,590,092 | 6/1971 | Uitti et al. | 260/674 SE |
| 3,702,295 | 11/1972 | Thompson | 208/321 |
| 3,714,033 | 1/1973 | Somekh et al. | 208/321 |
| 4,046,676 | 9/1977 | Asselin | 208/321 |
| 4,058,454 | 11/1977 | Asselin | 208/321 |
| 4,664,786 | 5/1987 | Forte et al. | 208/356 |
| 4,690,733 | 9/1987 | Forte et al. | 203/21 |
| 4,693,810 | 9/1987 | Forte et al. | 208/321 |
| 5,022,981 | 6/1991 | Forte | 585/808 |
| 5,073,669 | 12/1991 | Forte | 208/334 |

FOREIGN PATENT DOCUMENTS 0663914 5/1963 Canada .

OTHER PUBLICATIONS

UOP Sulfolane Process, Handbook of Petroleum Refining Processes, edited by Robert A. Meyers, pp. 8-53 to 8-60, published by McGraw-Hill Book Company, 1986.

Primary Examiner—Asok Pal
Assistant Examiner—P. Achutamurthy
Attorney, Agent, or Firm—Thomas K. McBride; John G. Tolomei

[57] ABSTRACT

A continuous solvent extraction process for the separation of aromatic hydrocarbons from a feedstock comprising aromatic and non-aromatic hydrocarbons provides more efficient heat utilization by using a lean solvent stream to heat the rich solvent stream as it passes from a primarily extractive stripping section to a section that primarily provides steam stripping. The feed stream is contacted with a lean solvent stream in an extraction zone to separate it into a raffinate stream comprising non-aromatic hydrocarbons and a first rich solvent stream comprising solvent, aromatic hydrocarbons and non-aromatic hydrocarbons. The first rich solvent stream passes to a first stripping zone section from which a first vapor stream is recovered and a second rich solvent stream is discharged. As the second rich solvent stream is passed to a second section of the stripping zone it is heated by heat exchange with the lean solvent stream that is recovered from the second stripping zone section. Heat exchange of the rich solvent with the lean solvent between stripping sections removes substantially more heat from the lean solvent stream than was previously removed when the lean solvent stream was used to heat stripping stream. The additional heat made available by this invention reduces the overall heat input and permits the use of low pressure steam to heat the stripping steam stream.

26 Claims, 3 Drawing Sheets

PROCESS FOR THE SEPARATION OF AROMATIC HYDROCARBONS WITH ENERGY REDISTRIBUTION

FIELD OF THE INVENTION

This invention relates to a continuous solvent extraction-steam-distillation process for the recovery of aromatic hydrocarbons from a feedstream containing aromatic hydrocarbons and non-aromatic hydrocarbons. More particularly, the subject invention relates to the redistribution of heat used within the process.

BACKGROUND OF THE INVENTION

Conventional processes for the recovery of high purity aromatic hydrocarbons such as benzene, toluene and xylenes (BTX) from various hydrocarbon feedstocks including catalytic reformate, hydrogenated pyrolysis gasoline, etc., utilize an aromatic selective solvent. Typically, in the practice of such processes, a hydrocarbon feed mixture is contacted in an extraction zone with an aqueous solvent composition which selectively dissolves the aromatic components from the hydrocarbon feedstock, thereby forming a raffinate phase comprising one or more non-aromatic hydrocarbons, and an extract phase comprising solvent having aromatic components dissolved therein.

An important consideration in the design and operation of an aromatic extraction process beyond the recovery and the purity of the products is the operating cost. Excluding labor and capital charges, the major component of the operating cost is the energy requirements of the process. Because the products produced from this process are generally not finished products, but are often intermediate components for the blending of finished fuels and for the production of petrochemicals, any reduction in processing costs can translate into a significant economic advantage. An example of the energy costs for a conventional process for this application appeared in a discussion of the UOP Sulfolane Process which may be found on pages 8-53 to 8-60 in a book edited by Robert A. Meyers, entitled *Handbook of Petroleum Refining Processses*, published by McGraw-Hill Book Company, in 1986. In Table 8.4-1 on page 8-60 of this reference, the processing costs are presented for a 10,000 (B/D) barrel per day Sulfolane Unit producing 6,000 B/D of BTX extract. The energy costs, comprising steam, electric power and cooling water amounted to 83% of the total processing cost on a daily basis, expressed in monitory units. Solvent make-up charges were 2%. Labor and maintenance costs made up the remaining 15%.

In commercial practice the amount of energy used by aromatics extraction processes range from 600-900 BTU's (British Thermal Units) per pound of aromatic material extracted. When one considers that the recovery of aromatic hydrocarbons involves the use of three major material cycles, typically hydrocarbon, water, and solvent, there are numerous possibilities within the process for the management of energy as these materials are vaporized and condensed to affect the separation.

A number of examples have been developed to achieve energy savings using continuous solvent extraction-steam-distillation for the recovery of aromatic hydrocarbons. Representative examples are believed to be presented in U.S. Pat. Nos. 4,690,733; 4,693,810 and 4,664,786. The U.S. Pat. No. 4,690,733, issued to Forte et al., shows an aromatics extraction process segment wherein high pressure steam is fed to a steam ejector and the resulting steam is employed in a first heat exchanger to provide heat to reboil a distillation column for the recovery of lean solvent and in a second heat exchanger to transfer heat from the recovered lean solvent to the condensate from the first heat exchanger before returning the condensate to the steam ejector to complete the steam generation cycle. The process is claimed to lower energy costs by reducing reflux to feed ratios in the extractor and lowering solvent recirculation rates. Capital costs are increased by the addition of the steam ejector and an additional heat exchange is required over conventional practice.

In the patent to Forte et al. (U.S. Pat. No. 4,693,810), the stripping water is divided into two streams. One stream is passed to a motive steam generator to vaporize the water and then passed to a steam ejector. The second stream is passed to a heat exchanger wherein heat is transferred from a lean solvent stream to vaporize all of the stripping water rather than just a portion and return the water vapor to the stripping column by means of the steam ejector. Capital costs are increased by the cost of the steam generator, steam ejector, and additional heat exchanger.

In the patent to Forte et al. (U.S. Pat. No. 4,664,786) stripping water is recycled to a steam distillation zone while heat recovered from an overhead stream is used to vaporize the stripping water using a motive steam generator to pump stripping water vapors into the stripping column.

Other processes for producing high purity aromatics are described in U.S. Pat. No. 3,714,033, and U.S. Ser. No. 408,827, allowed Jan. 16, 1991. These processes provide for the use of a single distillation column wherein both extractive distillation and a steam stripping occur. The patent discloses the preferred use of a polyalkylene glycol solvent in a temperature range of from about 100° C. (212° F.) to about 200° C. (392° F.) to provide a high purity aromatics product.

One more process for producing high purity aromatics is described in U.S. Pat. No. 4,058,454 and provides for the use of extractive and steam distillation in separate columns. A particularly suitable class of solvents for use in the above-identified patent are those commonly referred to as the sulfolane type. The process utilizes an extraction temperature, with a sulfolane solvent, in the range of from about 80° to about 400° F. and can provide a high purity aromatic product.

U.S. Pat. No. 3,590,092 discloses a method for aromatic hydrocarbon recovery that utilizes a single column wherein a side-cut vapor fraction comprising aromatic hydrocarbons and a minor quantity of solvent is withdrawn and introduced into a separate rectifying zone maintained under rectifying conditions, to provide a relatively solvent free aromatic extract product.

U.S. Pat. No. 3,702,295 discloses a method for aromatic hydrocarbon recovery that also utilizes the single column, vapor side-cut approach. However, this method differs from that disclosed in U.S. Pat. No. 3,590,092 in that the rectification zone is refluxed with the aqueous phase from the overhead condensate, instead of the hydrocarbon phase. Also, the bottoms fraction from the rectification zone is introduced to an intermediate section in the stripped column instead of the lower section.

Another aromatic hydrocarbon recovery method that uses a single column to provide two stripping sections is shown in U.S. Ser. No. 321,033, allowed Jan. 28, 1991. This arrangement uses a separate rectification column for purification of the aromatic product, but teaches that the rectification zone may be incorporated into the column.

Overall energy requirements of the process can be significantly reduced by minimizing the amount of heat withdrawn from the process to the environment as in cooling, or condensing of process streams. The condenser duty translates into the amount of energy that cannot be recovered, that is lost or taken out of the process. By lowering the temperature of the lean solvent, the selectivity of the solvent is improved and the amount of non-aromatics extracted with the aromatics is reduced, reducing the overall energy consumption.

Another way in which energy requirements can be reduced is by the utilization of less expensive heat sources. Many solvent extraction processes have arrangements that need high pressure steam to provide effective heating. Arrangements that permit the substitution of low pressure steam for heating—refiners generally view low pressure steam streams as waste heat—will offer significant savings over processes that need high pressure steam.

SUMMARY OF THE INVENTION

An object of this invention is to improve the redistribution of the of heat in a process for the recovery of aromatic hydrocarbons.

Another object of this invention is to reduce the amount of recycle to an extraction zone.

Yet another object of this invention is to provide solvent-extraction arrangement that facilitates the use of low pressure steam.

A yet further object of this invention is to reduce the flashing of rich solvent in a stripping zone.

This invention reduces the energy consumed by a series of two distillation zones in an aromatic solvent extraction process by transferring heat from a lean solvent stream to a rich solvent stream via a closed heat exchange loop or an interheater as the rich solvent stream passes from one distillation zone to the other. In addition, heat exchange of lean solvent in the manner of this invention decreases the temperatures of the feeds to the distillation zones which surprisingly reduces the amount of recycle comprising light non-aromatic hydrocarbons returned to an extraction zone. Using the lean solvent in this manner to reduce recycle to extraction zone can account for up to 50% or more of the energy savings. Lower stripping water rates resulting from the heating of the rich solvent between the distillation zones accounts for most of the additional energy savings. Lower stripping water requirements and the addition of heat from the lean solvent stream between the two distillation sections allows the use of typically cheap heat from low pressure steam to vaporize the stripping water and provide stripping steam for the process.

Accordingly in one embodiment, this invention is a continuous solvent extraction process for the separation of aromatic hydrocarbons from a feedstock comprising aromatic and non-aromatic hydrocarbons. The feedstock is contacted with a first lean solvent stream and a recycle stream in an extraction zone at extraction conditions. The feedstock is separated into a raffinate stream comprising non-aromatic hydrocarbons and a first rich solvent stream comprising solvent, aromatic hydrocarbons and non-aromatic hydrocarbons. The rich solvent stream is passed through a stripping zone and contacted with a stripping steam stream at stripping conditions in a first section of the stripping zone. A first vapor stream is recovered from the first stripping zone section and a second rich solvent stream is discharged from the first stripping zone section. The mixed hydrocarbon phase comprising non-aromatic hydrocarbons and aromatic hydrocarbons is separated from the first vapor stream and passed to the extraction zone as the recycle stream. The second rich solvent stream is passed to a second section of the stripping zone and contacted with a stripping steam stream. A second vapor stream is discharged from the second stripping zone section and a second lean solvent stream is withdrawn from the second stripping zone section. An aromatic product stream is recovered from the second vapor stream. At least a portion of the second lean solvent stream is reboiled and returned to the second stripping zone section. A second portion of the lean solvent stream is cooled to produce the first lean solvent stream by transferring heat from the second lean solvent stream to the second rich solvent stream as it passes from the first section to the second section of the stripping zone.

In another aspect of this invention, the second vapor stream is passed to a solvent recovery zone and contacted therein with a stripping steam stream. A third vapor stream comprising aromatic hydrocarbons and water is withdrawn from the solvent recovery zone and the aromatic product stream is recovered from the third vapor stream while a third lean solvent stream is discharged from the solvent recovery zone.

In a further aspect of this invention, the first rich solvent stream is heated by heat exchange with the first lean solvent stream before the first rich solvent stream enters the stripping zone.

In a yet further aspect of this invention, the stripping steam stream that enters the second section of the stripping zone is produced by heating a stripping water stream with a steam stream having a pressure of less than 50 psig.

DETAILED DESCRIPTION OF THE INVENTION

Figure 1:
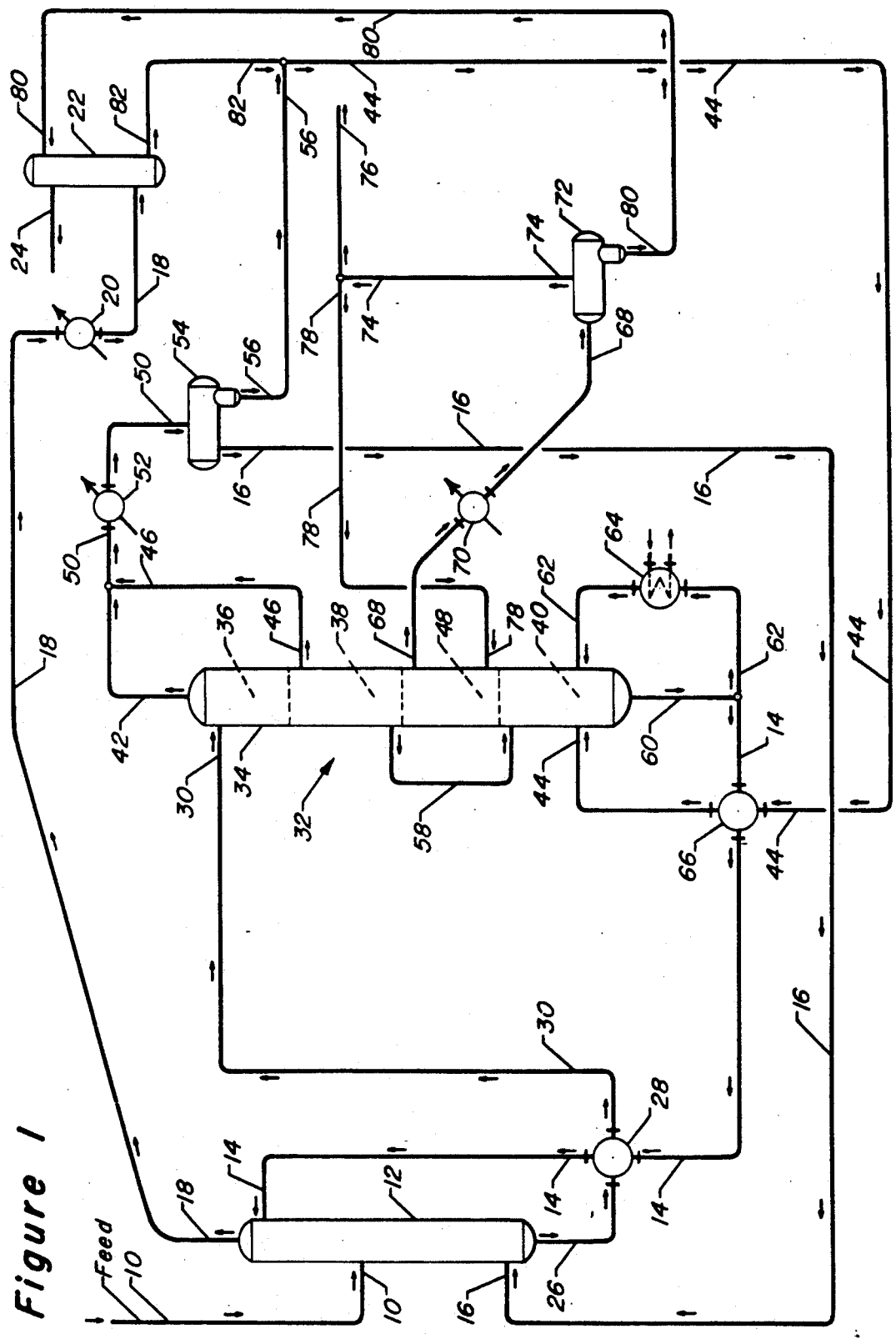
FIG. 1 is a schematic flow diagram of a process that does not incorporate the arrangement of this invention.

Hydrocarbon feedstocks suitable for utilization in the method of the present invention include many different aromatic-non-aromatic mixtures having a substantially high enough concentration of aromatic hydrocarbons to economically justify the recovery of the aromatic hydrocarbons as a separate product stream. The present invention is particularly applicable to hydrocarbon feed mixtures containing at least 15% by weight aromatic hydrocarbons. Typical aromatic feedstock charged to an extraction step will contain from about 25% to about 80% by weight aromatic hydrocarbons with aromatic hydrocarbon concentrations as high as 98% being suitable in some instances. A suitable carbon range for the hydrocarbon feedstock is from about 5 carbon atoms per molecule to about 20 carbon atoms per molecule, and preferably from 5 to 12 carbon atoms per molecule.

One suitable source of hydrocarbon feedstock is a depentanized fraction from the effluent from a conventional catalytic reforming process unit for the reforming of a naphtha feedstock. Another suitable source of feedstock is the liquid by-product from a pyrolysis gasoline unit which has been hydrotreated to saturate olefins and diolefins, thereby producing an aromatic hydrocarbon concentrate suitable for the solvent extraction technique described herein.

A preferred feedstock for use in the present invention is one recovered from a catalytic reforming unit, comprises single ring aromatic hydrocarbons of the $C_6$-$C_{10}$ range which are also mixed with corresponding boiling range paraffins and naphthenes which are present in the product from a catalytic reforming unit.

Solvent compositions which may be utilized in the practice of the present invention are those selected from the classes which have high selectivity for aromatic hydrocarbons. These aromatic selective solvents generally contain one or more organic compounds containing in their molecule at least one polar group, such as a hydroxyl, amino, cyano, carboxyl or nitro radical. In order to be effective, the organic compounds of the solvent composition having the polar radical must have a boiling point substantially greater than the boiling point of water since water is typically included in the solvent composition for enhancing its selectivity. In general, the solvent must also have a boiling point greater than the end boiling point of the aromatic component to be extracted from the hydrocarbon feed mixture.

Organic compounds suitable for use as part of the solvent composition are preferably selected from the group of those organic-containing compounds which include the aliphatic and cyclic alcohols, cyclic monomeric sulfones, the glycols and glycol ethers, as well as the glycol esters and glycol ether esters. The mono- and poly-alkylene glycols in which the alkylene group contains from 2 to 3 carbon atoms, such as ethylene glycol, diethylene glycol, triethylene glycol, and tetraethylene glycol, propylene glycol, dipropylene glycol, and tripropylene glycol, as well as the methyl, ethyl, propyl and butyl ethers of the glycol hydroxyl groups and the acetic acid esters and mixtures of the above, constitute a satisfactory class of organic solvents useful in admixture with water as the solvent composition for use in the present invention.

Some of these solvents, when combined with other cosolvents, can provide mixed extraction solvents having desirable properties. When such mixed solvents are utilized, the preferred solvents are the low molecular weight polyalkylene glycols of the formula:

wherein n is an integer from 1 to 5 and is preferably the integer of 1 or 2; m is an integer having a value of 1 or greater, preferably between about 2 to about 20 and most preferably between about 3 and about 8; and wherein $R_1$, $R_2$ and $R_3$ may be hydrogen, alkyl, aryl, aralkyl or alkylaryl and are preferably hydrogen and alkyl having between 1 and about 10 carbon atoms and most preferably are hydrogen. Examples of the polyalkylene glycol solvents employable herein are diethylene glcol, triethylene glycol, 1,3-butylene glycol, 1,2-butylene glycol, 1,5-pentaethylene glycol, and mixtures thereof and the like. Preferred solvents are diethylene glycol, triethylene glycol, tetraethylene glycol being most preferred. When a "cosolvent" component is employed herein such is preferably a glycol ether of the formula:

wherein $R_4$, $R_5$, $R_6$ and $R_7$ may be hydrogen alkyl, aryl, aralkyl, alkylaryl and mixtures thereof with the provisio that $R_4$ or $R_7$ are not both hydrogen. The value of x is an integer from 1 to 5, preferably 1 or 2 and y may be an integer from 1 to 10 and is preferably from 2 to 7, and most preferably from 2 to 5. $R_4$, $R_5$, $R_6$ and $R_7$ are preferably selected from the group consisting of hydrogen and alkyl having 1 to about 10 carbons with the provisio that $R_4$ and $R_7$ may not both be hydrogen and most preferably $R_4$ is alkyl having from 1 to 5 carbons and $R_5$, $R_6$ and $R_7$ are hydrogen. The mixture(s) of solvent and cosolvent is selected such that at least one solvent and one cosolvent are provided to form the mixed extraction solvent. The cosolvent generally comprises between about 0.1 and about 99 percent of the mixed extraction solvent, preferably between about 0.5 and about 80 percent and more preferably between about 5 and about 60 percent by weight based on the total weight of the mixed extraction solvent. The above-described mixed extraction solvents are fully disclosed in U.S. Pat. Nos. 4,498,980 and 4,781,820, hereby incorporated by reference.

Another typical aromatics-selective solvent utilized in commercial aromatic extraction processes which can be recovered in accordance with the practice of this invention, is commonly referred to as sulfolane (tetrahydrothiphene, 1-1 dioxide). Also employed are those sulfolane derivatives corresponding to the structural formula:

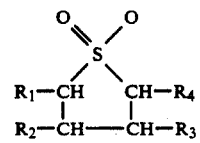

wherein $R_1$, $R_2$, $R_3$ and $R_4$ are independently selected from the group consisting of hydrogen, an alkyl radical containing from about 1 to about 10 carbon atoms, an aralkyl radical having from about 7 to about 12 carbon atoms, and an alkoxy radical having from about 1 to about 8 carbon atoms. Other solvents which may be included within this process are the sulfolenes, such as 2-sulfolene or 3-sulfolene which have the following structures:

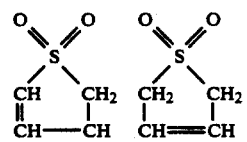

aromatics from non-aromatic hydrocarbons and which may be processed within the scope of the present invention are 2-methylsulfolane, 2,4-dimethylsulfolane, methyl-2-sulfonyl ether, N-aryl-3-sulfonylamine, 2-sulfonyl acetate, dimethylsulfoxide, N-methyl pyrrolidone, etc.

A particularly preferred solvent of the above-described sulfolane type has the following structural formula:

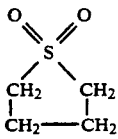

The aromatic selectivity of the solvent can usually be enhanced by the addition of water to the solvent. The solvents utilized in the practice of this invention could contain small quantities of water in order to increase the selectivity of the overall solvent phase for aromatic hydrocarbons without reducing substantially the solubility of the solvent of the solvent phase for aromatic hydrocarbons. Accordingly, the solvent composition of the present invention preferably contains from about 0.1% to about 20% by weight water and, preferably, about 0.5 to about 10% by weight depending upon the particular solvent utilized and the process conditions at which the extraction zone and the extractor-stripper are operated.

Aromatic hydrocarbons contained in the foregoing feedstocks are recovered by introducing the hydrocarbon feedstock into a solvent extraction zone maintained under solvent extraction conditions including the presence of an aromatic selective solvent of the type discussed. Solvent extraction conditions and techniques are generally well known to those trained in the art and vary, depending on the particular aromatic selective solvent utilized.

The solvent extraction zone provides an extract phase comprising solvent having aromatic hydrocarbons and a minor amount of non-aromatic hydrocarbons dissolved therein and a raffinate phase comprising non-aromatic hydrocarbons. Typically, the raffinate is water washed to remove any solvent which may be in solution and entrained therein. In the present invention, this water is preferably provided by the aqueous overhead condensate from a rectification zone as hereinafter described. Preferably, the extraction conditions utilized are correlated to maintain the solvent and hydrocarbons passed to the extraction zone in the liquid phase so as to embody a liquid phase solvent extraction. The conditions, apparatus, and mode of operation associated with the solvent extraction zone are well known to those trained in the art. For example, see U.S. Pat. Nos. 3,702,295; 3,714,003; 4,419,226; and 4,781,820, hereby incorporated by reference.

Also embodied within the solvent extraction zone is the concept of displacing heavier non-aromatic hydrocarbons from the extract phase at the lower end of the solvent extraction zone by utilizing the known technique of a recycling from the overhead of the stripping column hydrocarbon containing recycle at that point. By displacing the heavy non-aromatics with light non-aromatics, the resulting non-aromatics are more readily separable from the aromatics in the subsequent stripping zone to be discussed later. It is preferred that this recycle stream comprise relatively light non-aromatic hydrocarbons but significant quantities of aromatic hydrocarbons, i.e., 30% to 60% by weight, may be present in the recycle stream. The exact amount of recycle introduced into the lower section of the solvent extraction zone varies depending on the degree of non-aromatic hydrocarbon rejection desired in the extraction zone. Preferably, the recycle is at least 10% by volume of the extract phase so as to insure effective displacement of the heavy non-aromatic hydrocarbons from the extract phase into the raffinate. According to the process of the present invention at least a portion, if not all, of the light non-aromatic recycle required is provided by a non-aromatic fraction removed as overhead from an upper section of a hereinafter described stripping zone, usually comprising a single column. This fraction is withdrawn as a vapor and contains water (steam) which is preferably condensed and removed before the non-aromatics are passed as recycle to the solvent extraction zone, usually comprising a single extractor column. In accordance with the present invention, the preferred reflux to feed ratio is in the range of from about 0.2:1 to about 1.5:1 and the more preferred reflux to feed ratio is in the range of from about 0.2:1 to about 1.:1.

The solvent extraction zone is operated under conventional conditions including a temperature and a sufficiently elevated pressure to maintain the solvent, the recycle, and the hydrocarbon charge stream in the liquid phase. When utilizing a solvent such as sulfolane, suitable temperatures are about 80° F. to about 400° F., preferably about 175° F. to about 300° F., and suitable pressures are about atmospheric to about 400 psig, preferably about 50 to 150 psig. A more preferred pressure range for the solvent extraction zone is from 75 to 120 psig.

Solvent quantities should be sufficient to dissolve substantially all of the aromatic hydrocarbons present in the hydrocarbon feed to the extraction zone. Generally, to accomplish the extraction, the ratio of the mixed extraction solvent to hydrocarbon feed in the extractor zone is in the range from about 1 to about 20 parts by volume of mixed extraction solvent to one part by volume of feed, the ratio from about 2:1 to about 6:1 being preferred and the ratio from about 2:1 to about 4:1 being the most preferred. The broad range for the ratio of the mixed extraction solvent to hydrocarbon may be expanded upon depending on the particular solvent, cosolvent, relative amount of solvent to cosolvent, the amount of water in the mixed extraction solvent and the like. As used herein, the phrase "solvent to feed ratio" shall mean "mixed extraction solvent to feed ratio." The optimum solvent to feed ratio also depends upon whether high recovery (yield) or high purity (quality) is desired although the instant process will allow for both high recovery and high purity. Preferred are solvent to feed ratios, by volume, of about 1:1 to about 10:1, and most preferred are solvent to feed ratios of 2:1 to 6:1 when utilizing a $C_6$-$C_{10}$ range naphtha cut as feed.

The extract phase from the solvent extraction zone comprising solvent, aromatic hydrocarbons and contaminating non-aromatic hydrocarbons is introduced into a stripper zone. The stripping zone has at least two sections of distillation that remove the non-aromatic hydrocarbons from the solvent and aromatic hydrocarbons and the solvent from an aromatic product stream. These separations are accomplished by fractionation to remove essentially all of the contaminating amounts of non-aromatic hydrocarbons from the extract phase as a vapor fraction which is withdrawn from one stripping zone section. This vapor fraction comprises water (steam), non-aromatic hydrocarbons, and an amount of aromatic hydrocarbons. This vapor fraction is preferably cooled and condensed to form an aqueous phase and a hydrocarbon phase. This hydrocarbon phase is then recovered and passed to the lower section of the stripping zone to serve as the described light non-aromatic recycle and to recover the aromatic hydrocarbons contained in the original vapor fraction withdrawn from the upper portion of the stripping zone. The aromatic hydrocarbons recovered from this stripping section comprise a liquid in a rich solvent stream comprising aromatic hydrocarbons and solvent that are passed to another section of the stripping zone for the recovery of the aromatic product.

Typically, two types of column configurations are used in aromatics extraction processes to provide the stripping sections of the stripping zone. Both of these configurations are suitable for use with the present invention. In one type, a single column with a side-draw is employed to separate the rich solvent into an overhead stream rich in non-aromatic hydrocarbons, a side-draw stream rich in aromatic hydrocarbons, and a bottoms stream rich in mixed extraction solvent. In the other type, two columns are employed in such a manner that the first column is used as a first stripping section to separate the rich solvent into an overhead stream rich in non-aromatic hydrocarbons, and a bottoms stream containing mixed extraction solvent and aromatic hydrocarbons. The second column is used as a second stripping section to separate the bottoms stream from the first column into an overhead stream rich in aromatic hydrocarbons and a bottoms stream rich in mixed extraction solvent. For purposes of the present invention, both the upper section of the column in the single column configuration and the first column in the double column configuration can be considered as a first stripping section. Similarly, the lower section of the column in the single column configuration and the second column in the double column configuration can be considered as a second stripping section. Although the present invention is hereinafter described with reference to two stripping sections, the use of more than two sections is within the scope of the present invention.

The rich solvent phase is initially passed to the first stripping section wherein the non-aromatic hydrocarbons contained therein are separated from the aromatic hydrocarbons and the mixed extraction solvent. Preferably, the rich solvent is flashed prior to its introduction into the first stripping section in order to lower the pressure of the rich solvent to that of the first stripping section which is typically lower than the extraction zone. The flash material plus the overhead distillate removed from the first stripping section is condensed so as to comprise a recycle hydrocarbon phase and an aqueous phase. The aqueous phase often contains a small amount of mixed extraction solvent dissolved therein and accordingly is particularly suitable for use as stripping steam in the extractive stripping of the non-aromatic hydrocarbons from the aromatic hydrocarbons. The recycle hydrocarbon phase is then recycled to the extraction zone as hereinbefore described.

The bottoms from the first stripping section comprising aromatic hydrocarbons and the mixed extraction solvent are then passed to the second stripping section wherein the mixed extraction solvent is separated from the aromatic hydrocarbons. Preferably, steam stripping or a combination of steam stripping and reboiling are used in the second stripping section. The aromatic hydrocarbons are removed as a distillate (or side-draw in the single column configuration) and are thereafter either recovered as product or more typically treated by water washing or further distillation to remove any remaining mixed extraction solvent to low ppm levels.

When the three zone system is operated in three separate columns, the number of theoretical stages or trays required to achieve the degree of fractionation can easily be determined by one skilled in the art.

The number of stages selected for an individual process will depend somewhat upon the composition of the hydrocarbon feedstock and the content of aromatic hydrocarbons. The actual number of trays in each column will depend further upon the efficiency of the tray design employed for the separation. Typically, trays efficiencies for these separations range from 40–60%.

When the single column configuration is utilized, it is preferred to treat the distillate from the second stripping section, i.e., side draw, by rectification in a solvent recovery zone that usually comprises a small column, e.g., about 10 or fewer trays. This solvent recovery zone can be a separate column or an integral part of the main single column that contains the first and second stripping sections.

In the operation of the solvent recovery zone, the side draw distillate is passed to a lower section of the zone to separate therein the aromatic hydrocarbons from the mixed extraction solvent. This separation is accomplished by maintaining the solvent recovery zone under conditions including a temperature of about 100° F. to about 500° F., typically 200°–300° F. and a pressure of about 50 mm. Hg to about 25 psig, preferably 1 psig to about 15 psig, and withdrawing from an upper section of the solvent recovery zone a vapor fraction relatively free of mixed extraction solvent comprising aromatic hydrocarbons and water (steam). This vapor fraction is condensed and the aromatics recovered are essentially free of non-aromatics and mixed extraction solvent.

In one variation, the aromatics are removed as product from the solvent recovery zone and at least a portion of the aqueous phase of the condensate is returned to an upper section of the solvent recovery zone as reflux. Any remaining portions of the aqueous phase which are essentially solvent free, are preferably used to wash the raffinate from the extraction zone. At least a portion, and preferably all, of the bottoms from the solvent recovery zone which contain water and mixed extraction solvent are then passed to a lower section of the second stripping zone section to provide stripping medium.

In another variation, the aqueous phase of the condensate is not used to reflux the solvent recovery zone. Instead, at least a portion of the aromatic phase is returned to an upper section of the solvent recovery zone as reflux. Any remaining portions are preferably removed as product. The aqueous phase is, preferably, used to wash the raffinate. At least a portion, and preferably all, of the bottoms product of the solvent recovery zone are returned to an upper section of the second stripping zone section, preferably at about the same location, e.g., one tray below the location from which the side draw is withdrawn.

The solvent recovery zone described above can provide an aqueous phase that is essentially solvent free, i.e., low ppm levels. This aqueous phase can conveniently be used to wash the raffinate from the extraction zone in order to recover the mixed extraction solvent dissolved therein. Preferably, the spent raffinate wash water is used to provide at least a portion of the stripping medium used in the second stripping section.

At least a portion of the bottoms from the second stripping section comprise a lean solvent which is passed to the extraction zone as hereinbefore described. The term "lean solvent" is used herein to denote a mixed extraction solvent having a reduced aromatic hydrocarbon content relative to the rich solvent.

As is well known to those trained in the art, exact processing conditions are a function of a myriad of variables, particularly feed compositions, aromatic purity desired and aromatic recovery sought. However, the conditions to be utilized in the first stripper section of the type described are broadly within a temperature range of about 150° F. to about 500° F., typically 250°-380° F. at the bottom of the first stripper section and a pressure near atmospheric pressure. A near atmospheric pressure range for this invention shall mean about 500 mmHg absolute to about 50 psig and more preferably from about 1 psig to about 20 psig. Stripping medium, e.g. steam, is introduced to the second stripping section at a temperature between 100° F. and 280° F. The rich solvent feed is introduced to the second stripping section typically at a pressure at or above atmospheric pressure and a temperature of 180°-320° F. Based on the teaching herein, it is within the scope of one trained in the art to readily develop more specific processing conditions for a given feedstock.

This invention uses heat from the lean solvent stream of the second stripping section to heat the rich solvent as it passes from the first to the second stripping sections. It is also typical to heat the second stripping zone with a bottoms reboiler. Therefore the operating temperature of the second stripping zone will be a function of heat input from any reboiler and the heat transfer between the lean and rich solvents between the two stripping sections. As the rich solvent passes from the first to the second stripping zone it may be heated by an external heat exchanger through which the lean and rich solvent flow or an internal column heater such as a stab in reboiler. In the single column configuration the stab in reboiler may be located at the bottom of the first stripping zone section and preferably at or below the top of the second stripping zone section and more preferably at the very top of the second stripping zone section. Typically the rich solvent entering the second stripping zone will be heated to a temperature of from 200° to 300° F. by heat exchange with the lean solvent.

Stripping steam also provides another heat input into the column. As previously mentioned it was typical practice to obtain this steam by heat exchange with the lean solvent. Due to the heating of the rich solvent with the lean solvent stream, the overall quantity of stripping steam that enters the column can be reduced. In addition the stripping water is now vaporized into stripping steam with low pressure steam e.g. waste heat

EXAMPLES 1-3

Figure 2:
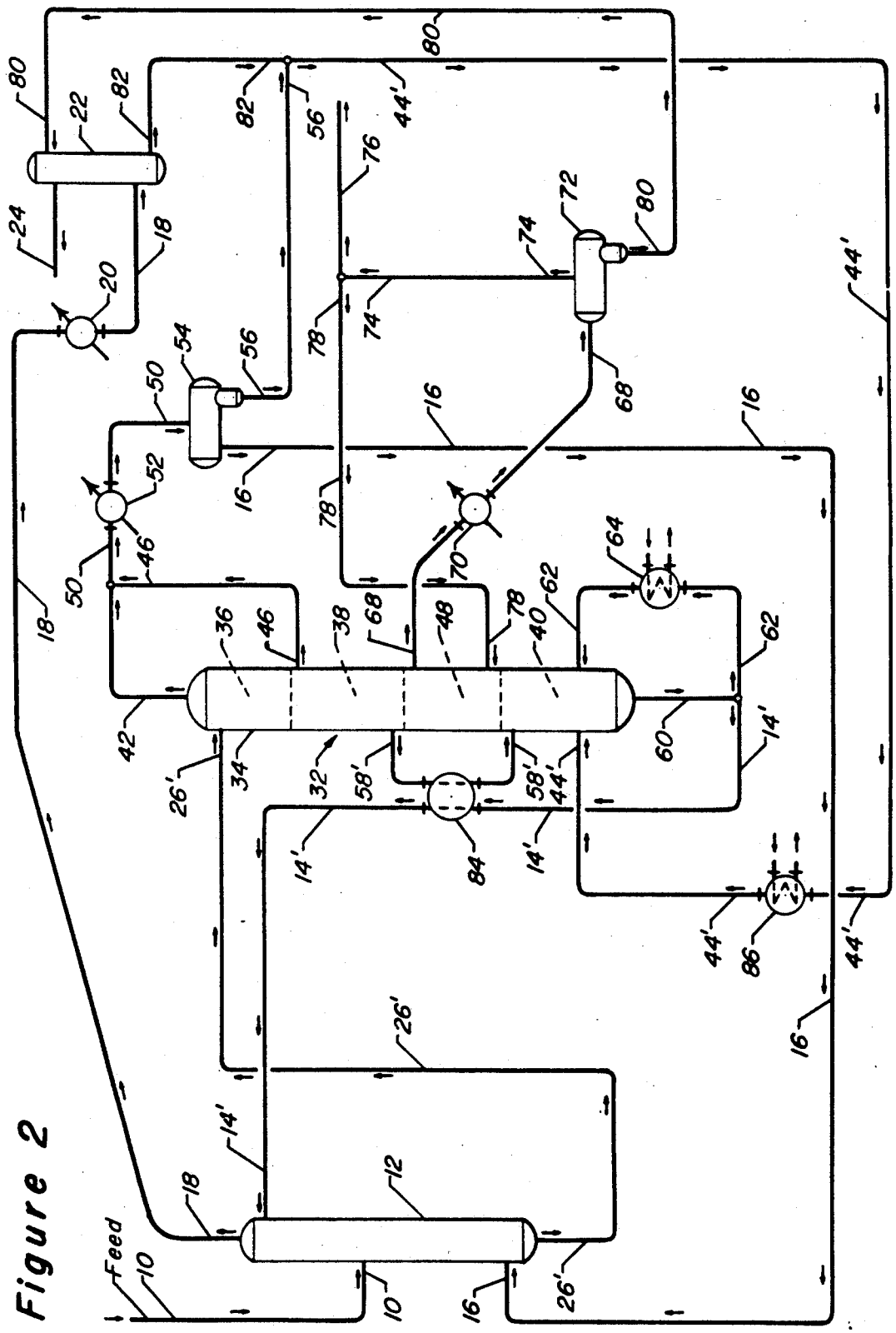
FIG. 2 is a schematic flow diagram showing a particular arrangement for the process of this invention.
Figure 3:
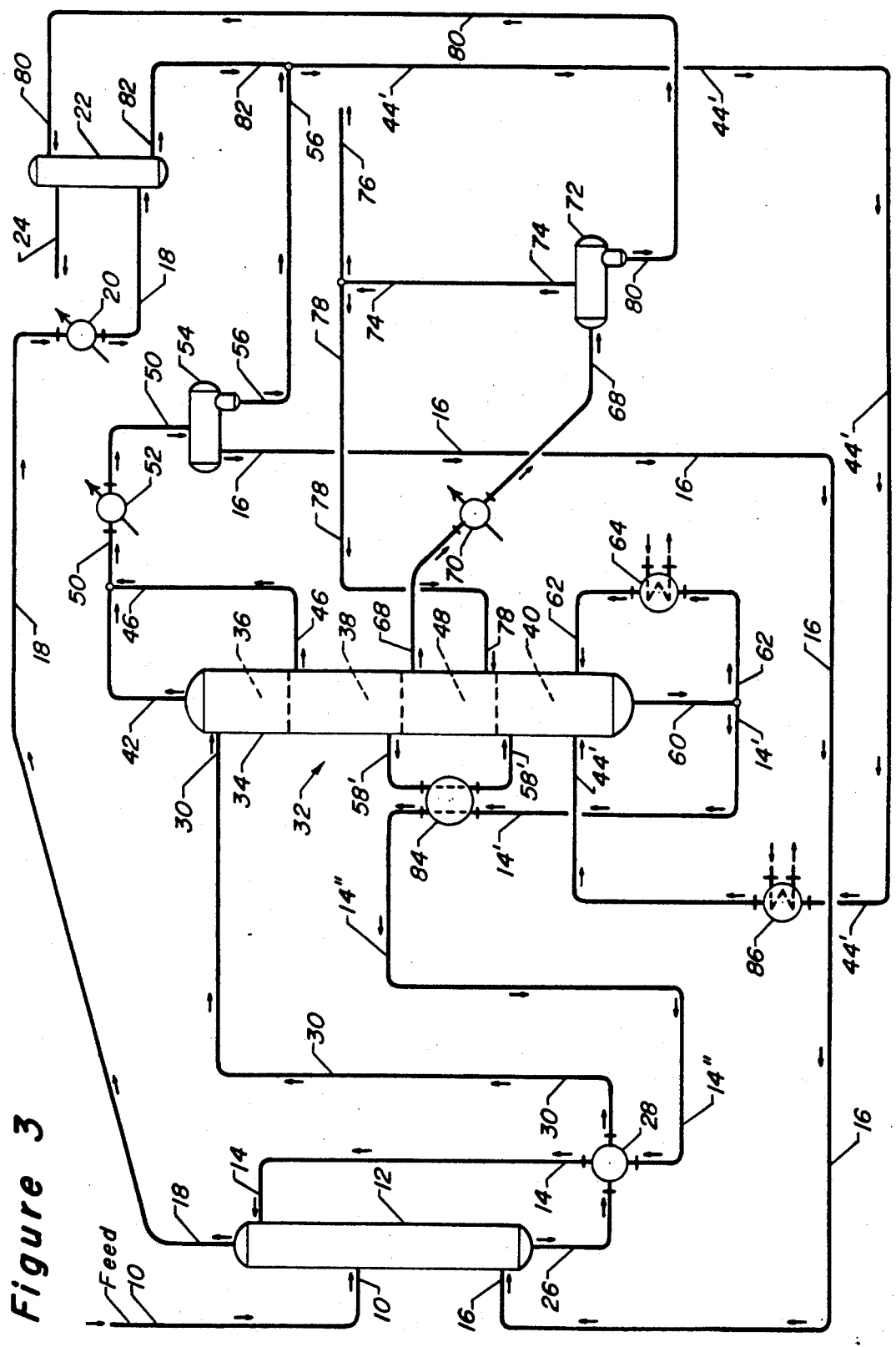
FIG. 3 is a schematic flow diagram showing a more limited arrangement for the process of this invention.

The further description of the method of this invention is presented with reference to a series of examples that reflect the operation of a process depicted in the attached schematics, FIG. 1, FIG. 2 and FIG. 3. FIGS. 2 and 3 represent preferred aspects of the invention and are not intended to be a limitation on the generally broad scope of the invention as set forth in the claims. Of necessity, some miscellaneous appurtenances including valves, pumps, separators, heat exchangers, reboilers, etc., have been eliminated. Only those vessels and lines necessary for a complete and clear understanding of the process of the present invention are illustrated, with any obvious modifications made by those possessing expertise in the art of aromatic solvent extraction. All of the examples use the feed described in Table I which enters the arrangement of each example at a rate of 94,900 lbs/hr. All of the examples are based on computer simulations that utilize process data to correlate results to actual operations.

TABLE I

| Components | Vol. % | Wt. % |
| --- | --- | --- |
| Benzene | 12.99 | 14.64 |
| Toluene | 44.02 | 49.09 |
| p-Xylene | 0.12 | 0.13 |
| Ethylbenzene | 0.22 | 0.25 |
| Total Aromatics | 57.35 | 64.11 |
| n-Pentane | 18.49 | 14.91 |
| n-Hexane | 15.04 | 12.63 |
| n-Heptane | 5.19 | 4.59 |
| n-Octane | 1.46 | 1.33 |
| n-Nonane | 0.02 | 0.02 |
| Total Paraffins | 40.20 | 33.48 |
| Cyclopentane | 1.12 | 1.11 |
| Cyclohexane | 0.44 | 0.44 |
| Methylcyclopentane | 0.53 | 0.51 |
| Methylcyclohexane | 0.34 | 0.34 |
| Total Naphthenes | 2.43 | 2.40 |
| 1-Hexane (olefins) | 0.02 | 0.02 |

EXAMPLE 1

FIG. 1 is a schematic flow diagram of a basic solvent-extraction arrangement that dose not utilize the teachings of the present invention. In the FIG. 1 the first and second stripping sections are contained within a single distillation column.

A $C_6$-$C_9$ cut of depentanized reformate containing aromatic and non-aromatic hydrocarbons is passed via line 10 to extractor 12 at a temperature of 75°-85° F. which is maintained at extraction conditions including a temperature in the range of from about 140° to about 190° F. and a pressure in the range of from about 75 to about 120 psig. Lean solvent enters the extractor 12 via line 14 at a solvent to feed weight ratio of about 3 to 1 and a temperature of from 170°-180° F. Reflux hydrocarbons enter the extractor 12, via line 16 at a reflux to feed ratio of about 0.5 and a temperature of 120°-140° F. A raffinate phase containing non-aromatic hydrocarbons and mixed extraction solvent is removed from extractor 12 via line 18. The mixed extraction solvent is thereafter recovered from the raffinate phase by cooling the raffinate phase in condensor 20 to separate a portion of the dissolved mixed extraction solvent out of solution in a raffinate wash column 22 from where the raffinate product is recovered by line 24.

A rich solvent phase, i.e., extract, containing aromatic hydrocarbons, non-aromatic hydrocarbons, solvent and water, is removed from extractor 12 via line 26 and passed through heat exchanger 28 to an upper section 34 of a distillation column 32 via line 30. The top of upper section 34 is a vaporizing chamber 36 which functions to flash off and vaporize a portion of the non-aromatic hydrocarbons contained in the rich solvent phase of line 30. Stripping section 34 also includes an extractive stripping portion 38. In the lower portion of column 32 is a second stripping section 40 wherein primarily steam stripping and reboiling occur.

In the operation of distillation column 32, the rich solvent phase, as previously mentioned, is introduced into flashing section 36 at superatmospheric pressure, e.g., 10 psig and a temperature of about 160 to about 210° F. Under these conditions, a portion of the non-aromatic hydrocarbons is flashed off and removed via line 42. The remainder of the extract phase now comprising mixed extraction solvent having the desired aromatic hydrocarbons dissolved therein, is passed into the distillation portion 38 wherein extractive and steam stripping operations take place. The stripping medium, e.g. steam comprising mixed extraction solvent, is first introduced to the lower section 40 of column 32 via line 44.

As aromatic hydrocarbons and mixed extraction solvent pass downward through column portion 38, extractive stripping of a non-aromatic and aromatic hydrocarbons takes place above a solvent recovery zone that occupies a central portion 48 of column 32. The remainder of non-aromatic hydrocarbons and stripping steam are withdrawn from column portion 38 by a sidecut 46. Sidecut stream 46 is combined with the flashed overhead of line 42 into a stream 50, cooled in condensor 52 and passed to a drum 54. Drum 54 separates a hydrocarbon phase from an aqueous phase. The hydrocarbon phase comprises non-aromatic and aromatic hydrocarbons that provide the recycle carried by line 16. The aqueous phase is withdrawn from drum 54 by a line 56 to ultimately provide a portion of the water for generating the stripping steam carried by line 44.

A line 58 carries bottoms from the first stripping section around solvent recovery zone 48 and into the second stripping section of the column 32. The bottoms from the first stripping section are rich in aromatic hydrocarbons and provide a second rich solvent stream. Primarily steam stripping occurs in the second stripping section. A bottoms stream comprising lean solvent is withdrawn by a line 60. The bottom of the section 40 operates at a temperature of about 300° to 320° F. Heat is supplied to section 40 by reboiling a portion of the column bottoms, carried by a line 62, in a reboiler 64. Reboiler 64 uses high pressure steam, 150 psig, to heat the contents of line 62 to a temperature of about 300° to 320° F. the remaining portion of the lean solvent from line 60 is returned to extractor 12 via line 14 after vaporizing at least part of the stripping water of line 44 into stripping steam in an exchanger 66.

Aromatic hydrocarbons and small amounts of solvent are carried upward by the second stripping section into the aromatic recovery zone 48. A sidecut line 68 withdraws a purified aromatic hydrocarbon stream and stripping steam from the top of solvent recovery zone 48. A condensor 70 condenses the sidecut line 68 which is transferred to a drum 72. A purified aromatic stream containing less than 2 ppm of solvent is withdrawn from drum 72 by a line 74. A product line 76 withdraws a portion of the purified aromatic hydrocarbons as product. The remainder of the purified aromatic product is returned to the solvent recovery zone 48 as reflux by a line 78 to a point below the withdrawl point of line 68.

The aqueous condensate from the sidecut drum 72 is passed via line 80 to the raffinate wash column 22. A line 82 carrying solvent containing wash water from column 22 is combined with the overhead aqueous condensate in line 56 from the first stripping section and passed to heat exchanger 66 via line 44 for use as stripping steam as hereinbefore described. Typically, the aqueous phase from line 80 is very low in solvent and provides clean wash water for the hereinbefore described raffinate washing.

Additional operational details of Example 1 are presented in Table II

EXAMPLE 2

Example 2 shows the operation of a solvent extraction zone that incorporates the teaching of this invention and has the arrangement as shown in FIG. 2. The details of the flow schemes FIGS. 1 and 2 are the same in many respects and only the differences between the flow schemes are set forth herein.

The solvent extraction zone operates in essentially the same manner as discussed with respect to FIG. 1. However the arrangement of FIG. 2 does not exchange the extract stream against the lean solvent stream. Instead the extract stream is transferred directly to the flash chamber 36 of column 32 by line 26'. After flashing and extractive stripping the second rich solvent stream passes to the second stripping section through a line 58' which is heat exchanged against the lean solvent stream carried by line 14' in a heat exchanger 84. The rich solvent stream is heated from a temperature of about 200° to 210° F. to a temperature of about 220° to 240° F. by contact with the lean solvent in exchanger 84 which heating in turn cools the lean solvent from a temperature of about 300° to 320° F. to a temperature of about 200° to 220° F. Heating of the rich solvent stream in exchanger 84 reduces the amount of stripping stream that must enter the second stripping section through a line 44'. The stream in line 44' was generated by heat exchange with 25 psig steam in a heat exchanger 86.

The absence of heat exchange between the lean solvent and the rich solvent raises the temperature of the lean solvent carried by line 14' into extractor 12 by about 40° F. but the temperature of the rich solvent carried by line 26' into column 32 is lowered by about 20° to 40° F. when compared to the temperatures of these streams in Example 1. The higher temperature of the lean solvent stream does not cause any substantial change in the recovery or purity of aromatic hydrocarbons as compared to Example 1. However, the lower temperature of the rich solvent stream 26' results in reduced flashing in stripper section 34 and lowering the recycle rate to the extraction zone. Thus, the results summarized in Table II show that a significant energy savings was obtained by the method of this invention over the method of Example 1. The energy savings obtained by the method of this invention total about 15% when compared to Example 1. Moreover, the fact that exchanger 86 used low pressure steam to supply a quarter the energy requirements of the process makes this energy savings much more dramatic since the energy of low pressure steam streams typically have an inherently low value.

EXAMPLE 3

The efficiency of the process can be further enhanced by the continued use of exchanger 28 to transfer heat between the lean and rich solvent streams as they pass to and from the extractor. Example 3 as illustrated in FIG. 3 represents such an operation where the rich solvent carried by line 26 is heat exchanged with lean solvent carried by line 14" in heat exchanger 28. As shown in FIG. 3 the lean solvent is cooled in exchanger 84 by heating the second rich solvent stream of line 58'. A line 14" carries the cooled lean solvent stream from exchanger 84 to exchanger 28. Passing the lean solvent through exchanger 28 in the arrangement of FIG. 3 again cools the lean solvent that enters the extractor to about the same temperature as the lean solvent that enters the extractor in Example 1. The additional heat exchange between the lean and rich solvent in Example 3 further increases the energy savings of the process over those obtained in Example 2. However, the addition of the exchanger adds capital expense which must be balanced against the long term energy savings.

TABLE II

| PROCESS VARIABLES | EXAMPLE 1 | EXAMPLE 3 | EXAMPLE 2 |
|---|---|---|---|
| EXTRACTOR COLUMN 12 | | | |
| Solvent/Feed, wt/wt | 2.82 | 2.78 | 2.80 |
| Reflux/Feed, wt/wt | 0.52 | 0.40 | 0.41 |
| Lean Solvent Temperature, °F. | 176 | 176 | 216 |
| Water in Lean Solvent wt % | 5.3 | 4.5 | 4.5 |
| STRIPPER COLUMN 32 | | | |
| Bottom Temperature, °F. | 310 | 310 | 310 |
| Stripping Water/Aromatics Ratio (wt) | 0.19 | 0.125 | 0.123 |
| Reboiler 64 Duty, MMBTU/hr | 36.6 | 22.6 | 23.3 |
| Exchanger 84 Duty, MMBTU/hr | none | 8.1 | 8.0 |
| Exchanger 66 Duty, MMBTU/hr | 11.1 | none | none |
| Exchanger 86, Duty, MMBTU/hr | none | 16.2 | 16.3 |
| Exchanger 28, Duty, MMBTU/hr | 12.1 | 6.5 | none |
| AROMATICS RECOVERY | | | |
| Benzene (wt %) | 99.93 | 99.96 | 99.97 |
| Toluene (wt %) | 99.87 | 99.87 | 99.86 |
| $C_8$ Aromatics (wt %) | 96.64 | 94.20 | 94.40 |
| PURITIES | | | |
| Benzene (99.6% min.) | 99.96 | 99.95 | 99.96 |
| Benzene NA (600 ppm max.) | 435 | 456 | 450 |
| PROCESS HEAT DUTY | | | |
| 150 psig Steam (MMBTU/hr) | 36.61 | 22.6 | 23.3 |
| 25 psig Steam (MMBTU/hr) | — | 8.1 | 8.0 |
| Total Duty in MMBTU/hr | 36.61 | 30.7 | 31.3 |
| Total Duty in MMBTU/lb arom. | 602 | 505 | 514 |
| Energy Reduction | | 16% | 15% |

I claim:

1. A continuous solvent extraction process for the separation of aromatic hydrocarbons from a feedstock comprising aromatic and non-aromatic hydrocarbons, said process comprising:
   (a) contacting said feedstock with a first lean solvent stream and a recycle stream in an extraction zone and at extraction conditions and separating said feedstock into a raffinate stream comprising non-aromatic hydrocarbons and a first rich solvent stream comprising solvent, aromatic hydrocarbons and non-aromatic hydrocarbons;
   (b) passing said rich solvent stream to a stripping zone, contacting said solvent stream with a stripping steam stream at stripping conditions in a first section of said stripping zone, recovering a first vapor stream from said first stripping zone section and discharging a second rich solvent stream from said first stripping zone section;
   (c) separating a mixed hydrocarbon phase comprising non-aromatic hydrocarbons and aromatic hydrocarbons from said first vapor stream and passing said mixed hydrocarbon phase to said extraction zone as said recycle stream;
   (d) passing said second rich solvent stream to a second section of said stripping zone, contacting said second rich solvent stream with a stripping steam stream in said second stripping zone section, discharging a second vapor stream from said second stripping zone section, and withdrawing a second lean solvent stream from said second stripping zone section;
   (e) recovering an aromatic product stream from said second vapor stream;
   (f) reboiling at least a portion of said second lean solvent stream and returning said reboiled portion to said second stripping zone section; and,
   (g) cooling a second portion of said second lean solvent stream and producing said first lean solvent stream by transferring heat from said portion of said second lean solvent stream to said second rich solvent stream as it passes from said first section to said second section of said stripping zone.

2. The process of claim 1 wherein said solvent comprises polyalkene glycol.

3. The process of claim 2 wherein said solvent comprises tetraethylene glycol.

4. The process of claim 1 wherein said solvent comprises a polyalkylene glycol of the formula:

wherein n is an integer from 1 to 5, m is an integer having a value of 1 or greater and $R_1$, $R_2$ and $R_3$ may each be hydrogen, alkyl, aryl, aralkyl, alkylaryl and mixtures thereof and a glycol ether of the formula:

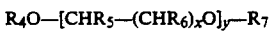

wherein $R_4$, $R_5$, $R_6$ and $R_7$ may each be hydrogen, alkyl, aryl, aralkyl, alkylaryl and mixtures thereof with the proviso that $R_4$ and $R_7$ are not both hydrogen; x is an integer from 1 to 5; and y may be an integer from 2 to 10.

5. The process of claim 4 wherein said solvent consists essentially of a polyalkylene glycol selected from the class consisting of diethylene glycol, triethylene glycol, tetraethylene glycol and mixtures thereof and a glycol ether selected from the class consisting of methoxytriglycol, ethoxytriglycol, butoxytriglycol, methoxytetraglycol and ethoxytetraglycol and mixtures thereof wherein the glycol either comprises between about 0.1 and 99 percentage by weight of the mixed extraction solvent.

6. The process of claim 5 wherein the polyalkylene glycol is tetraethylene glycol and the glycol ether is methoxytriglycol.

7. The process of claim 1 wherein said solvent comprises a sulfolane derivative solvent.

8. The process of claim 1 wherein said solvent comprises sulfolane.

9. The process of claim 1 wherein said second vapor stream is passed to a solvent recovery zone and contacted with a reflux stream in said solvent recovery zone, a third vapor stream comprising aromatic hydrocarbons and water from said solvent recovery zone is withdrawn, said aromatic product stream is recovered from said third vapor stream and a third lean solvent stream is discharged from said solvent recovery zone.

10. The process of claim 1 wherein said first rich solvent stream is heated by heat exchange with said first lean solvent stream before said first rich solvent stream enters said stripping zone.

11. The process according to claim 1 wherein the aromatic product stream comprising benzene, toluene and xylene isomers.

12. The process according to claim 1 wherein the aromatic hydrocarbons are separated to produce a toluene fraction and said fraction is blended with other hydrocarbon components to produce finished motor gasoline.

13. The process of claim 1 wherein the stripping steam stream that enters the second section of said stripping zone is produced by heating a stripping water stream to a stripping steam temperature using a steam stream having a pressure of less than 50 psig.

14. The process of claim 13 wherein said stripping steam stream is heated by heat exchange with a low pressure steam stream having a pressure of less than 25 psig.

15. The process of claim 1 wherein said second lean solvent stream heats said second rich solvent stream to a temperature of from 200° to 300° F.

16. The process of claim 10 wherein said first lean solvent stream is cooled to a temperature of 150° to 300° F. by heat exchange with said first rich solvent stream.

17. The process of claim 13 wherein a second wash water stream is separated from said second vapor stream and at least a portion of said first or second wash water stream is heated to provide stripping steam stream.

18. A continuous solvent extraction process for the separation of aromatic hydrocarbons from a feedstock comprising aromatic and non-aromatic hydrocarbons, said process comprising:
(a) contacting said feedstock with a first lean solvent stream and a recycle stream in an extraction zone and at extraction conditions and separating said feedstock into a raffinate stream comprising non-aromatic hydrocarbons and a first rich solvent stream comprising solvent, aromatic hydrocarbons and non aromatic hydrocarbons;
(b) passing said rich solvent stream to a stripping zone having a first stripping section and flashing said first rich solvent stream in a first region of said first stripping section, reducing the pressure of said first rich solvent stream in said flash chamber and recovering first vapor stream from said flash chamber;
(c) passing the remainder of said first rich solvent stream through a second region of said first stripping section, contacting said remaining rich solvent stream with a stripping steam stream at stripping conditions, recovering a second vapor stream from said first stripping zone section and discharging a second rich solvent stream from said first stripping zone section;
(d) combining said first and second vapor streams, separating a water stream and a mixed hydrocarbon phase comprising non-aromatic hydrocarbons and aromatic hydrocarbons from said combined vapor stream, and passing said mixed hydrocarbon phase to said extraction zone as said recycle stream;
(e) passing said second rich solvent stream to a second stripping section of said stripping zone, contacting said second rich solvent stream with a stripping steam stream in said second stripping zone section, discharging a third vapor stream from said second stripping zone section, and withdrawing a second lean solvent stream from said second stripping zone section;
f) passing said third vapor stream to a solvent recovery zone, contacting said third vapor stream with a reflux stream in said solvent recovery zone, withdrawing a fourth vapor stream comprising aromatic hydrocarbons and water from said solvent recovery zone, and discharging a third lean solvent stream from said solvent recovery zone;
(g) separating said fourth vapor stream into a second water stream and an aromatic stream, refluxing a portion of said aromatic stream to said solvent recovery zone and recovering an aromatic product stream from said aromatic stream;
(h) reboiling a portion of said second lean solvent stream and returning said reboiled stream to said solvent recovery zone; and
(i) cooling a second portion of said second lean solvent stream to produce said first lean solvent stream by transferring heat from said second portion of said second lean solvent stream to said second rich solvent stream as it passes from said first to said second section of said stripping zone to heat said second rich solvent stream to a temperature in a range of from 200° to 300° F.

19. The process of claim 18 wherein said solvent comprises a polyalkylene glycol of the formula:

wherein n is an integer from 1 to 5, m is an integer having a value of 1 or greater and $R_1$, $R_2$ and $R_3$ may each be hydrogen, alkyl, aryl, aralkyl, alkylaryl and mixtures thereof and a glycol ether of the formula:

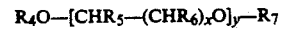

wherein $R_4$, $R_5$, $R_6$ and $R_7$ may each be hydrogen, alkyl, aryl, aralkyl, alkylaryl and mixtures thereof with the proviso that $R_4$ and $R_7$ are not both hydrogen; x is an integer from 1 to 5; and y may be an integer from 2 to 10.

20. The process of claim 18 wherein said solvent comprises a sulfolane derivative solvent.

21. The process of claim 18 wherein said first rich solvent stream is heated by heat exchange with said first lean solvent stream as said rich solvent stream passes from said extraction zone to said first stripper zone.

22. The process of claim 18 wherein said solvent recovery zone is located above said second stripping zone in a common column and said third lean solvent stream is discharged downwardly from said solvent recovery zone into said second stripping zone.

23. The process of claim 18 wherein said stripping steam stream that enters said second stripping section of said stripping zone is generated by heating water with steam having a pressure of less than 50 psig.

24. The process of claim 23 wherein said second water stream and said raffinate stream are passed to a raffinate wash column, a third water stream is discharged from said wash column, and said third and first water streams are combined and passed to heat exchanger to generate said stripping steam stream.

25. The process of claim 18 wherein said first stripping section, said second stripping section, and solvent recovery section are in a single column.

26. A continuous solvent extraction process for the separation of aromatic hydrocarbons from a feedstock comprising aromatic and non-aromatic hydrocarbons, said process comprising:
(a) contacting said feedstock with a first lean solvent stream and a recycle stream in an extraction zone and at extraction conditions and separating said feedstock into a raffinate stream comprising non-aromatic hydrocarbons and a first rich solvent stream comprising solvent, aromatic hydrocarbons and non aromatic hydrocarbons;

(b) heating said first rich solvent stream by heat exchange with said first lean solvent stream in a first heat exchanger;

(c) passing said rich solvent stream from said first heat exchanger to a stripping column having a first stripping section located in an upper portion of said column and flashing said first rich solvent stream in a upper region of said first stripping section, reducing the pressure of said first rich solvent stream in said flash chamber and recovering first vapor stream from said flash chamber;

(d) passing the remainder of said first rich solvent stream through a lower region of said first stripping section, contacting said remaining rich solvent stream with a stripping steam stream at stripping conditions, recovering a second vapor stream from said first stripping zone section and discharging a second rich solvent stream from said first stripping zone section;

(e) combining said first and second vapor streams, separating a water stream and a mixed hydrocarbon phase comprising non-aromatic hydrocarbons and aromatic hydrocarbons from said combined vapor stream, and passing said mixed hydrocarbon phase to said extraction zone as said recycle stream;

(f) passing said second rich solvent stream to a second stripping section located in the bottom of said stripping column, contacting said second rich solvent stream with a stripping steam stream in said second stripping section, discharging a third vapor stream from the top of said second stripping section, and withdrawing a second lean solvent stream from the bottom said second stripping section;

(g) passing said third vapor stream upwardly into a solvent recovery zone located in the middle of said stripping column, contacting said third vapor stream with reflux stream from said second stripping zone section in said solvent recovery zone, withdrawing a fourth vapor stream comprising aromatic hydrocarbons and water as a sidecut from said solvent recovery zone, and downwardly discharging a third lean solvent stream from said solvent recovery zone into said second stripping section;

(h) separating said fourth vapor stream into a second water stream and an aromatic stream, refluxing a portion of said aromatic stream to said solvent recovery zone and recovering an aromatic product stream from said aromatic stream;

(i) passing said second water stream and said raffinate stream to a raffinate wash column, withdrawing a raffinate product from said raffinate wash column and withdrawing a third water stream from said raffinate wash column;

(j) combining said first and third water streams, heating said first and water streams by heat exchange in a second heat exchanger with steam having a pressure of less than 50 psig;

(k) reboiling a first portion of said second lean solvent stream and returning said reboiled stream to said solvent recovery zone; and (l) cooling a second portion of said second lean solvent stream to produce said first lean solvent stream by transferring heat from said second portion of said second lean solvent stream to said second rich solvent stream as it passes from said first to said second section of said stripping column to heat said second lean solvent stream to a temperature in a range of from 200° to 300° F.

* * * * *